US008323166B2

(12) United States Patent
Haines et al.

(10) Patent No.: US 8,323,166 B2
(45) Date of Patent: Dec. 4, 2012

(54) PHARMACEUTICAL PACKAGE HAVING A MULTI-FUNCTIONAL SURFACE AND A METHOD OF PREPARING A MULTI-FUNCTIONAL SURFACE ON A PHARMACEUTICAL PACKAGE

(75) Inventors: Daniel Haines, Lake Ariel, PA (US); Luis Burzio, Wentzville, MO (US); Matthias Bicker, Mainz (DE); Horst Koller, Uznach (CH); Jasmina Marjanovic, St. Gallen (CH); Robert Hormes, Wolfertswil (CH)

(73) Assignee: Schott AG, Mainz (DE)

( * ) Notice: Subject to any disclaimer, the term of this patent is extended or adjusted under 35 U.S.C. 154(b) by 502 days.

(21) Appl. No.: 12/160,259

(22) PCT Filed: Jan. 9, 2007

(86) PCT No.: PCT/US2007/000301
§ 371 (c)(1),
(2), (4) Date: Dec. 17, 2008

(87) PCT Pub. No.: WO2007/081814
PCT Pub. Date: Jul. 19, 2007

(65) Prior Publication Data
US 2010/0044268 A1 Feb. 25, 2010

Related U.S. Application Data

(60) Provisional application No. 60/757,863, filed on Jan. 11, 2006, provisional application No. 60/795,596, filed on Apr. 28, 2006.

(51) Int. Cl.
*B65B 3/00* (2006.01)

(52) U.S. Cl. .......... 493/220; 493/110; 53/131.1; 53/411

(58) Field of Classification Search .............. 53/410, 53/411, 128.1, 131.1, 41; 604/265, 172; 493/110, 220
See application file for complete search history.

(56) References Cited

U.S. PATENT DOCUMENTS

| | | | | |
|---|---|---|---|---|
| 4,595,625 A * | 6/1986 | Crass et al. | ................. | 428/215 |
| 4,734,318 A * | 3/1988 | Crass et al. | ................. | 428/216 |
| 5,169,720 A * | 12/1992 | Braatz et al. | ............... | 428/423.1 |
| 5,736,251 A * | 4/1998 | Pinchuk | ...................... | 428/447 |
| 6,024,220 A * | 2/2000 | Smith et al. | .................. | 206/484 |
| 6,196,960 B1 * | 3/2001 | Owensby | ...................... | 493/220 |
| 6,443,980 B1 | 9/2002 | Wang et al. | | |
| 6,765,069 B2 * | 7/2004 | Zamora et al. | ............... | 525/404 |
| 6,908,681 B2 | 6/2005 | Terry et al. | | |
| 7,115,321 B2 * | 10/2006 | Soerens et al. | ............... | 428/500 |
| 2001/0027299 A1 * | 10/2001 | Yang et al. | .................... | 604/265 |
| 2002/0068180 A1 | 6/2002 | Yang et al. | | |
| 2003/0108588 A1 | 6/2003 | Chen et al. | | |
| 2003/0215644 A1 | 11/2003 | Deshpande et al. | | |
| 2005/0070996 A1 | 3/2005 | Dinh et al. | | |

(Continued)

*Primary Examiner* — Christopher Harmon
(74) *Attorney, Agent, or Firm* — Millen, White, Zelano, Branigan, P.C.

(57) ABSTRACT

The present invention relates to a multi-functional pharmaceutical package surface and a method of preparing a multi-functional pharmaceutical package surface. In particular, the present invention relates to a pharmaceutical package having a protein deterrent and lubricious surface and methods of preparing said surface by applying coatings directly to the pharmaceutical package that (a) reduce the adsorption of proteins onto pharmaceutical packaging while not affecting the activity of the protein solution and (b) provide a lubricious surface. The pharmaceutical package surface may also contain a barrier coating. Coatings can be deposited on a variety of pharmaceutical packaging materials and configurations by various methods.

37 Claims, 3 Drawing Sheets

U.S. PATENT DOCUMENTS

Figure 1:
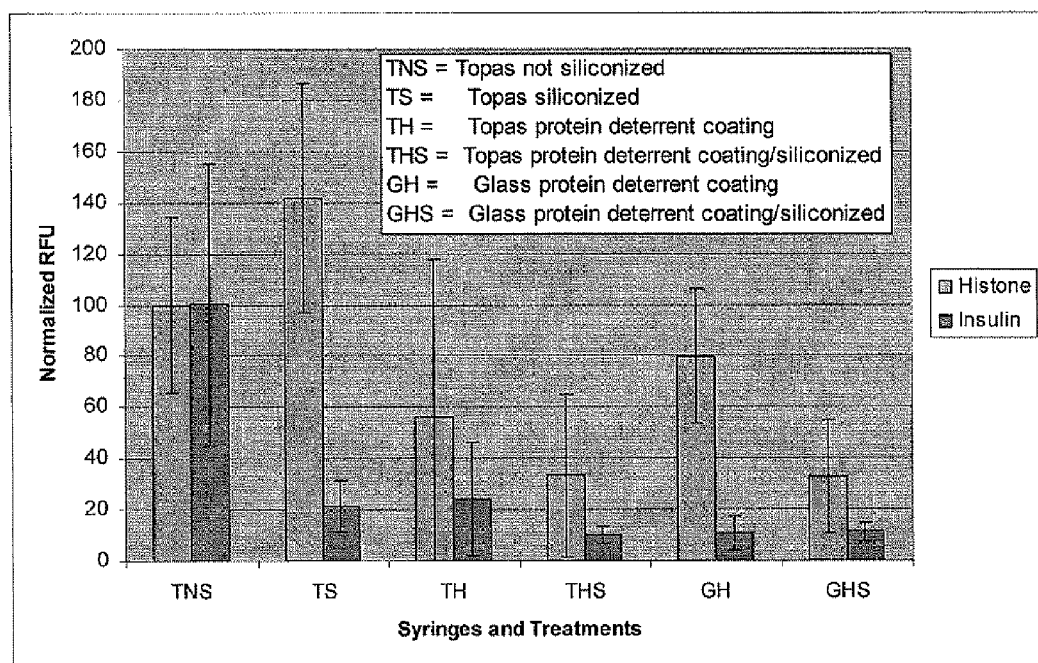

| | | |
|---|---|---|
| 2005/0191331 A1 | 9/2005 | Hunter et al. |
| 2005/0288398 A1 | 12/2005 | Messersmith et al. |
| 2006/0093771 A1* | 5/2006 | Rypacek et al. ............ 428/36.91 |
| 2007/0187280 A1* | 8/2007 | Haines et al. ................. 206/528 |

* cited by examiner

PHARMACEUTICAL PACKAGE HAVING A MULTI-FUNCTIONAL SURFACE AND A METHOD OF PREPARING A MULTI-FUNCTIONAL SURFACE ON A PHARMACEUTICAL PACKAGE

This application claims the benefit of the filing date of U.S. Provisional Application Ser. No. 60/757,863 filed Jan. 11, 2006 and U.S. Provisional Application Ser. No. 60/795,596 filed Apr. 28, 2006.

INTRODUCTION

One significant growth area in the pharmaceutical industry is the increasing prevalence of protein based drug formulations in lyophilized and parental form. As proteins have a strong affinity for the surface of native pharmaceutical packaging materials (e.g., glass and polymers), this results in the loss of product by interaction of the protein to the surface leading to permanent immobilization and/or denaturation. For higher concentration protein based drugs like insulin the accepted solutions to reduce protein adsorption are 1) to compensate for the protein loss by overfilling—using a higher than needed concentration and/or volume to provide enough product to passivate the surface and still maintain the required dosage, 2) to include additives such as sacrificial proteins and/or surfactants in the drug formulation to reduce adsorption, and 3) siliconization of the packaging material (S. M. Shaw, M. J. C. Crabbe *Biochem J.* 1994, 304, 121-129). The addition of proteins from non-recombinant sources generates concern with the possibility of protein bound diseases such as Creutzfeld-Jakob (M. M. Robinson et al Dev. Bio. Stand. 1996, 88, 237-241). With the advent of more specialized (expensive) protein based drugs, the increased costs to overfill the packaging container are undesirable both to the manufacturer and consumer. For example, a higher concentration drug protein such as Humulin N™ (recombinantly produced insulin made by Eli Lily) is used at a 300-400 µg/mL concentration with 10 mL/dose at a cost of $25.00 (pricing Feb. 6, 2006 at www.GetCanadianDrugs.com) while a lower concentration drug protein such as Avonex™ (recombinantly produced interferon$\alpha i\beta$ made by Biogen) is used at a 60 µg/mL concentration with a 0.5 mL/dose at a cost of $350.00; pricing Feb. 6, 2006 at www.GetCanadianDrugs.com). Starting with a conservative estimate of 5% protein adsorption one would have the potential to decrease the cost by $1.25 and $17.50/dose for Humulin™ and Avonex™, respectively, if one could provide a coating that minimizes protein loss.

The adsorption of proteins to a surface depends on a variety of factors: substrate surface chemistry (functional groups present on a native surface or coating thereon), surface conditions, such as roughness, the structure of the protein (molecular weight, distribution of amino acids, isoelectric point), and the excipients (binders, disintegrants, diluents, suspension and dispersing agents) present in the protein formulations. The chemically heterogeneous structure of proteins allows for surface interaction through hydrogen bonding and a variety of interaction mechanisms (ionic, hydrophobic, Van der Waals interactions, entanglement, etc.). To mitigate binding through these mechanisms most protein drug formulators rely on various excipients such as carbohydrates (e.g., trehalose, sucrose), buffers systems (e.g., phosphate, tris, citrate) and surfactants (e.g., polysorbate-80 or polysorbate-20). Though these approaches may be well established they are not always possible for different proteins whose activities may be modified by the addition of excipients resulting in the need for each formulation to be tested for stability of the protein drug contained in the package and the effect of the protein adsorption quantified in terms of loss of protein and protein activity.

Another approach to deter proteins binding to the surface of the package is the application of coatings to the package surface, provided it is feasible in a pharmaceutical packaging scenario (low cost, sterilizable by one or more of the accepted methods of autoclaving/EtO exposure/gamma irradiation/electron beam irradiation, non-toxic, 2-3 year stability, 100% coating deposition verifiable, etc.). A large body of literature has established a set of generally accepted theoretical parameters (Ostuni E., Chapman R. G., Holmin R. E., Takayama S., Whitesides G. M. Langmuir 2001, 17, 5605-5620) that determine if a surface is likely to deter protein adsorption. In general, a surface that is non-ionic, hydrophilic and hydrogen bond accepting is considered an ideal surface to repel protein adsorption at the liquid/solid interface. The coating should also be sterically hindering to the proteins interaction with the pharmaceutical package and/or component(s) surface (glass, polymer, copolymer, metal, alloys) to avoid not only adsorption, but also denaturation. Other theories have been proposed in the literature to explain the ability of certain coatings to reduce protein adsorption—for instance, see Gombotz et al (Gombotz W. R., Wang G. H., Horbett T. A., Hoffmann A. S. J. Biomed. Mater. Res. 1991, 12, 1547-1562), who postulate that the effectiveness of a coating (in this case polyethylene oxide) to structure water at the coating/water interface region influences the ability of a coating to reduce protein adsorption.

There is a wealth of general knowledge regarding surfaces and or coatings that resist protein adsorption. A non-exhaustive list include polyethylene oxide/glycol-like and other coatings deposited via plasma assisted chemical vapor deposition that deter protein adsorption—see, for example, Erika E. Johnston E. E., Bryers J. D., Ratner B. D. Langmuir 2005, 21, 870-881; Sardella E., Gristina R., Senesi G. S., d'Agostino R., Favia P. Plasma Process. Polym. 2004, 1, 63-72; Shen M., Martinson L., Wagner M. S., Castner D. G., Ratner B. D., Horbett T. A. J. Biomater. Sci. Polymer Edn. 2002, 13, 367-390; Shen M., Pan Y. V., Wagner M. S., Hauch K. D., Castner D. G., Ratner B. D., Horbett T. A. J. Biomater. Sci. Polymer Edn. 2001, 12, 961-978; U.S. Pat. No. 5,153,072; Lopez G. P., Ratner B. D. J. Polym. Sci. A—Polym. Chem. 1992, 30, 2415-2425; and U.S. Pat. No. 5,002,794. For (derivatized) alkanethiol coatings deposited that deter protein adsorption see, for example, Li L. Y., Chen S. F., Ratner B. D., Jiang S. Y. J. Phys. Chem. B 2005, 104, 2934-2941; Chirakul P., Pérez-Luna V. H., Owen H., López G. P. Langmuir 2002, 18, 4324-4330; Prime K. L., Whitesides G. M. J. Am. Chem. Soc. 1993, 115, 10714-10721; Pale-Grosdemange C., Simon F. S., Prime K. L., Whitesides G. M. J. Am. Chem. Soc. 1991, 113, 12-20. For organosilane coatings that deter protein adsorption see, for example, Seigers C., Biesalski M., Haag R. Chem. Eur. J. 2004, 10, 2831-2838; US 2003/0092879; Yang Z., Galloway J. A., Yu H. Langmuir 1999, 15, 8405-8411; Lee S. W., Laibinis P. E. Biomaterials 1998, 19, 1660-1675; and U.S. Pat. No. 6,235,340. For hydrogel coatings that deter protein adsorption see, for example, U.S. Pat. No. 6,844,028. For poly-L-lysine/polyethylene glycol coatings that deter protein adsorption see, for example, US 2002/0128234; Huang N. P., Michel R., Voros J., Textor M., Hofer R., Rossi A., Elbert D. L., Hubbell J. A., Spencer N. D. Langmuir 2001, 17, 489-498; Kenausis G. L. Vörös J., Elbert D. L., Huang N., Hofer R., Ruiz-Taylor L., Textor M., Hubbell J. A., Spencer N. D. J. Phys. Chem. B 2000, 104, 3298-3309. For polyethylene oxide graft coatings see, for example, Sofia S. J., Premnath. V., Merrill E. W. Macromolecules 1998, 31, 5059-5070.

These examples represent but are not an exhaustive compilation of the large number of available surface treatment and/or coating possibilities.

Currently, no commercially available pharmaceutical package (native or coated) contains all of the favorable protein deterring characteristics described above, but tends to have a few desirable ones while still having some that promote protein adsorption. While glass (borosilicate, soda-lime, etc.) is hydrophilic and hydrogen bond accepting, it is highly ionic and has no steric hindrance to deter protein binding. The high density of negative charges under liquid formulation conditions (pH 5-9) on the surface will promote the ionic binding of positively charged residues on the proteins (i.e. lysine, histidine, and the amino terminus). The siliconization of glass to passivate the surface and provide lubricity in syringes results in a relatively non-ionic surface that is sterically blocked, but the silicone oil renders the surface very hydrophobic while decreasing its hydrogen bond accepting ability. Silicone oil treatment can also result in the generation of unwanted particulate matter in syringes as silicone droplets leave the surface and enter the solution. Hydrophobic surfaces tend to exclude water and facilitate the adsorption of proteins. The hydrophobicity of the environment the proteins encounter can also lead to protein denaturation as the hydrophobic core of the proteins seeks to interact with the surface and unfold it's native structure to obtain a minimum free energy conformation. Hydrophobic coatings containing fluorine with anti-adherency properties for solutions/suspensions containing medicinally relevant particles/agglomerates have been prepared previously by plasma enhanced chemical vapor deposition—see, for example, U.S. Pat. No. 6,599,594.

For drugs delivered in liquid form, lubrication of the delivery system (i.e. syringe) is an important function of the packaging system. The lubricated syringe format is the format most likely to be utilized for high cost protein-based drugs. The currently accepted method of lubrication uses various formulations of silicones to provide lubrication of the syringe barrel as it moves down the syringe body. This method of lubrication, however, suffers from the "stick-slip" problem. It is difficult to accurately dispense from siliconized syringes, as there is a breakaway force that the user needs to apply to overcome the initial sticking forces between the barrel and body and also a sliding force that the user needs to maintain while dispensing. If the user stops before dispensing the entire volume of solution or makes multiple dispensings from the same syringe the user again needs to overcome the breakaway force. Without being restricted by theory, it is believed that the origin of the breakaway force is caused by migration of the lubricant (silicone) away from the contact points between sliding surfaces due to the compression force of the plunger and syringe body. Efforts have been made to reduce and/or eliminate the stick-slip problem. For example U.S. Pat. No. 6,645,635 discloses a tetrafluoroethylene barrier coating for use with stoppers while U.S. Pat. No. 6,582,823 discloses the use of perfluoropolyethers compounds as a wear-resistant coating that could be used as a silicone-free lubricant.

The stability of a drug formulation prior to delivery can be affected by many factors—the major factors are formulation dependent and packaging dependent. The primary factor affecting drug stability is the interaction of the drug formulation with leachables/extractables or permeating gas species during storage. During storage, glass, polymer, elastomer, and metal packaging components may release species (e.g. $Na^+$, $K^+$, $Al_3^+$, $SiOH^{n-}_{4-n}$, stearic acid, calcium stearate, 2,6-di-tert-butyl-4-methylphenol) that interact with various components of the drug formulation or allow the permeation of gaseous species such as oxygen or carbon dioxide. For example, when storing water for injection in Type 1 glass alkali ion exchange causes the pH to change. Barrier coatings, such as $SiO_2$, to reduce the exposure of drug solutions or components thereof to ion exchange and/or various gases, have been produced via plasma enhanced chemical vapor deposition methods to minimize the release of glass constituents into drug formulations. See for example, DE 196 29 877 M. Walther et al.; EP 08 210 79 M Walther et al.; DE 44 38 359 M. Walther et al.; EP 07 094 85 M. Walther et al. and DE 296 09 958 M. Walther et al.

With the increasing number of biotherapeutic drugs reaching the market and in development (recombinant therapeutic proteins Datamonitor 2004, DMHC 1975) there exists a need for multi-functional pharmaceutical packaging surfaces that incorporate multiple beneficial functions to enhance drug stability (i.e., multi-functional), especially for sensitive protein-solution based drugs. Currently there are no pharmaceutical packaging components that provide a combination of minimized protein loss, lubrication, and barrier properties for the storage and delivery of drug formulations. It is the goal of this invention to provide two or more multiple beneficial functions for pharmaceutical packaging components by the sequential application of two or more coatings.

Although the primary purpose of this patent application is to provide a packaging solution for protein-based drugs that are packaged in a liquid formulation, the technology described herein can also be applied to other biopharmaceuticals such as nucleic acids, small molecules, polynucleotides (e.g., DNA, RNA, pDNA, etc., oligonucleotides), protein/nucleic acid complexes (e.g., viral particles for gene therapy) that are either in a liquid ("solution") or solid state ("lyophilized") format, etc. by straightforward extension.

SUMMARY OF THE INVENTION

The present invention relates to a multifunctional pharmaceutical package (or synonymously, a pharmaceutical container) having a surface coated with a lubricious coating and a coating that minimizes protein loss (i.e., protein deterrent coating). Preferred lubricious coatings include, for example, silicone oil or a fluorinated polymer lubricant coating. Preferred coatings that minimize protein loss include, for example, a hydrogel coating or a polyether coating. The multi-functional pharmaceutical package surface may also include, for example, a barrier layer coating. The functional coatings may be deposited onto the pharmaceutical package surface by methods conventionally known in the art such as, for example, methods taught in H. K. Pulker *Coatings on Glass* $2^{nd}$ Ed. 1999 Elsevier, Amsterdam-hereby incorporated by reference. Preferred methods are spray coating, dip coating, chemical vapor deposition, plasma assisted chemical vapor deposition, sputtering, ion plating, and evaporation. Each coating may be applied by the same method or by different methods. Any pharmaceutical package that comes in contact with a pharmaceutical or biotechnological substance or formulation can be multi-functionally coated. Preferred pharmaceutical package surfaces which may be multi-functionally coated include vials, plastic-coated vials, syringes, plastic coated syringes, ampoules, plastic coated ampoules, cartridges, bottles, plastic coated bottles, pouches, pumps, sprayers, stoppers, needles, plungers, caps, stents, catheters and implants, and additional components thereof. Additional coatings, which provide functional benefits, include optical coatings that provide transparency or opacity, coating which provide strength, adhesion coatings, break resistant coatings and/or barrier coatings such as, for example, $SiO_2$. Pharmaceutical packaging substrates made from glass (e.g., Type 1, a silicate, a borate, a borosilicate, a phosphate, a soda-lime silicate, Type 2, Type 3, and colored versions thereof to protect formulations from various forms of electromagnetic radiation), acrylic, polycarbonate, polyester, polypropylene, polyacetal, polystyrene, polyamide, polyacrylamide, polyimide, polyolefin, cyclic olefin copolymers (e.g. Topas™-COC), rubber, elastomers, thermosetting polymers, thermoplastic polymers, metals, or alloys are contemplated. In particular, pharmaceutical packaging materials that have a siliconized or silanized surface are contemplated.

In comparison to uncoated pharmaceutical package substrates the protein deterrent-coated substrates of the invention reduce the adsorption of protein to the surface by more than about 25%. Preferred coatings reduce the adsorption of proteins to the surface by more than about 50% and particularly preferred coatings that minimize protein loss reduce the adsorption of proteins to the surface by more than about 75%. Although written in terms of proteins, other macromolecules that are deterred include naturally occurring or synthetically prepared biomolecules or a derivative thereof (e.g., nucleic acid, polynucleotide, protein, carbohydrate, or protein/nucleic acid complex) in solution or solid state.

Polyethers, such as, diglyme, triglyme, tetraglyme, pentaglyme, hexaglyme, or functionalized derivatives thereof are particularly suitable coatings that minimize protein loss, as are hydrogels. Particularly preferred polyethers are disclosed in U.S. Pat. No. 5,153,072 and U.S. Pat. No. 5,002,794, which are incorporated by reference. Other suitable coatings that minimize protein loss and coating precursors are the compounds disclosed in DE 196 29 877; EP 08 210 79; DE 44 38 359; UP 07 094 85 and DE 296 09 958, all of which are incorporated by reference.

Hydrogel coatings are also preferred coatings that minimize protein loss (i.e., protein deterrent). Particularly preferred hydrogels are disclosed in U.S. Pat. No. 6,844,028 and US 2005/0100675, which are incorporated by reference. These hydrogel formulations are typically composed of a mixture of solvent, a matrix forming component, a crosslinking component, and an active component made up of a binding group, a spacer group, and a functional group such as, for example, alkoxide (—OR where R is an alkyl group) or a secondary amine.

Lubricious coatings that are particularly suitable include silicone oils such as those taught in U.S. Pat. No. 5,736,251, U.S. Pat. Nos. 5,338,312, and 6,461,334, all of which are incorporated by reference. Also preferred are hydrophobic coatings containing fluorine such as those taught in U.S. Pat. No. 6,599,594, which is hereby incorporated by reference. Particularly suitable fluorinated polymer lubricious coatings include perfluorinated polyethers or fluorinated hydrocarbons. In comparison to uncoated pharmaceutical package substrates the coated substrates of the invention increase the lubricity of the surface by more than about 25%. Preferred lubricious coatings increase the lubricity of the surface by more than about 50% and particularly preferred lubricious coatings increase the lubricity of the surface by more than about 75%. Preferably, the lubricious coating does not detract from the protein deterrent functions of the coating that minimizes protein loss.

Particularly suitable barrier coatings which reduce the exposure of drug solutions or components thereof to ion exchange and/or various gases include, for example, those disclosed in DE 196 29 877 M. Walther et al.; EP 08 210 79 M Walther et al.; DE 44 38 359 M. Walther et al.; EP 07 094 85 M. Walther et al. and DE 296 09 958 M. Walther et al, all of which are incorporated by reference.

Suitable coatings may be deposited in sequence. Preferably, the coating that minimizes protein loss may be applied over an existing coating such as a lubricious coating, a barrier layer (e.g., $SiO_2$, $TiO_2$, $ZrO_2$ or $Al_2O_3$), an adhesion layer, or an optical layer. Alternatively, the preferred coating that minimizes protein loss may be applied under a coating such as a lubricious coating, a barrier layer (e.g., $SiO_2$, $TiO_2$, $ZrO_2$ or $Al_2O_3$), an adhesion layer, or an optical layer.

The invention also relates to methods of preparing a multi-functional pharmaceutical package surface coated with a lubricious coating and a coating that minimizes protein loss (i.e. protein deterrent coating) and optionally a barrier coating, an adhesion layer, an optical coating and/or a strength coating

BRIEF DESCRIPTIONS OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein:

FIG. 1: Protein adsorption of fluorescently labeled insulin and histone results for syringes coated with a lubricious coating and a coating that minimizes protein loss.

Figure 2:
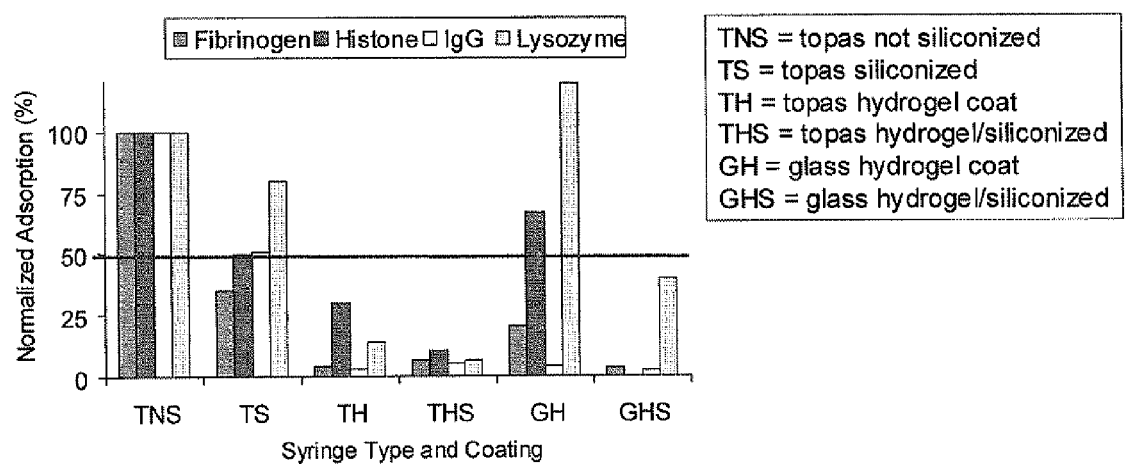

FIG. 2: Protein adsorption of fluorescently labeled insulin, histone, IgG, and lysozyme results for syringes coated with a lubricious coating and a coating that minimizes protein loss.

Figure 3:
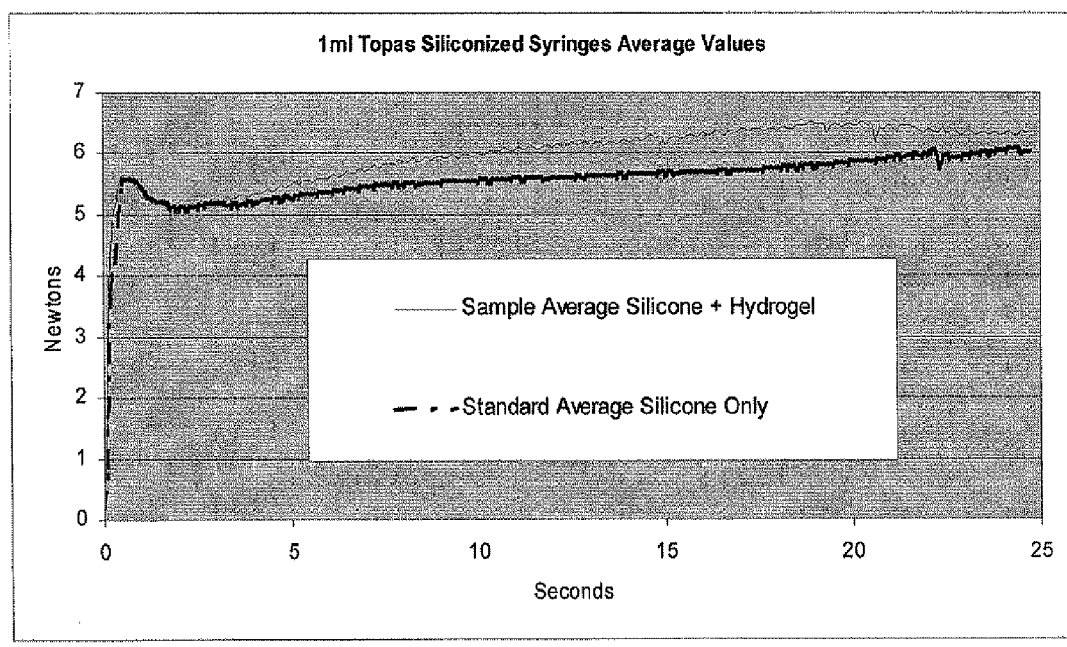

FIG. 3: Breakaway and sliding force comparison of syringes with a silicone oil coating vs. syringes with silicone oil and a coating that minimizes protein loss.

DETAILED DESCRIPTION OF THE INVENTION

As used herein, protein solution refers to a particular protein of interest in the presence of (typically) an aqueous solution that may contain various additives, which can also have an effect on the adsorption of the proteins to the surface. Typical protein solutions to be tested contain pharmaceutically relevant moieties such as cells, tissues, and derivatives thereof. Among the proteins are included any polyaminoacid chain, peptides, protein fragments and different types of proteins (e.g., structural, membrane, enzymes, antigens, monoclonal antibodies; polyclonal antibodies, ligands, receptors) produced naturally or recombinantly, as well as the derivatives of these compounds, etc. Specific protein drugs include antibodies (e.g. Remicade and ReoPro from Centocor; Herceptin from Genentech; Mylotarg from Wyeth, Synagis from MedImmune), enzymes (e.g. Pulmozyme from Genentech; Cerezyme from Genzyme), recombinant hormones (e.g., Protropin from Genentech, Novolin from Zymogenetics, Humulin from Lilly), recombinant interferon (e.g., Actimmune from InterMune Pharmaceutical; Avonex from BiogenIdec, Betaseron from Chiron; Infergen from Amgen; Intron A from Schering-Plough; Roferon from Hoffman-La Roche), recombinant blood clotting cascade factors (e.g., TNKase from Genentech; Retavase from Centocor; Refacto from Genetics Institute; Kogenate from Bayer) and recombinant erythropoietin (e.g., Epogen from Amgen; Procrit from J&J), and vaccines (e.g., Engerix-B from GSK; Recombivax HB from Merck & Co.).

The term "multi-functional" refers to two or more beneficial desirable properties provided by coatings for pharmaceutical packaging used for the storage and delivery of drug formulations. These include, but are not limited to, coatings which minimize protein adsorption (i.e., protein deterrent coating), provide lubrication, provide a barrier to leachables, extractables, and permeating gases, provide optical transparency, provide optical opacity, provide break resistance and are compatible with sterilization methods.

The term "pharmaceutical package" as used herein means any container or medical device or component(s) thereof that comes in contact with a pharmaceutical, biological or biotechnological substance or formulation in solution or solid state. Examples include vials, plastic-coated vials, syringes, plastic coated syringes, ampoules, plastic coated ampoules, cartridges, bottles, plastic coated bottles, pouches, pumps, sprayers, stoppers, needles, plungers, caps, catheters, stents, implants, and components thereof which come in contact with proteins.

With regards to the coatings that minimize protein loss, the coating precursors may be from any chemical family. Preferably, the coating will be universal, and as such deter the adsorption of all potential protein formulations. In some instances, this will not be the case and an initial analysis of some of the proteins properties (e.g., pI, charged residues, modifications such as glycosilations, hydrophobicity and/or hydrophilicity) could lead to specific modifications to be included in the coating formulation. Analysis of the surface (e.g., energy, roughness, charge, and functional groups) of various packaging components could also lead to specific characteristics and/or modifications of the coating formulation to reduce the adsorption of the protein. With this in mind, preferred coating families are glycols, ethers, esters, alcohols, methacrylates, silanes and derivatized members thereof. Especially preferred coating precursors for use in the present invention include compounds containing the elements C, H and O; polyethylene glycols, glycol ethers, commonly known as glymes (e.g., monoglyme, ethyl glyme, diglyme, ethyl diglyme, triglyme, butyl diglyme, tetraglyme, pentaglyme, hexaglyme and their respective corresponding monoalkyl ethers) and functionalized derivatizes such as, for example, polyethylene glycol with an end functionalized silane. The coating thickness can range from a monolayer to 1000 nm. Preferably the protein deterrent coating is from about 1 to 1000 nm, most preferably the protein deterrent coating is from about 1 to 500 nm and coatings of about 1 to 250 nm are most preferred.

Hydrogel coatings are another class of particularly preferred coating that minimizes protein loss. Preferred hydrogels and methods of applying the hydrogels to surfaces are disclosed in U.S. Pat. No. 6,844,028, US 2004-0115721 and US 2005-0100675, which are all incorporated by reference. These hydrogel formulations are typically composed of a mixture of solvent(s), a matrix forming component, a crosslinking component, and an active component, the active component consisting of a binding group, a spacer group, and a functional group. Particularly preferred hydrogels comprise a $NH_2$-PEG-silane or methoxy-PEG-silane active component.

The coatings that minimize protein loss (e.g., hydrogel or polyether) may be deposited over other functional coatings such as, for example, a barrier coating (e.g., an oxides such as $SiO_2$) or a lubricious coating. Alternatively, the coating that minimizes protein loss (e.g., hydrogel or polyether) may be deposited under other functional coatings such as a barrier coatings or a lubricious coating.

There are numerous types of known lubricants, such as non-siliconized oils (i.e. vegetable oils), fats, waxes, and hydrophilic polymers such as those disclosed in U.S. Pat. No. 6,723,350. With regards to the lubricious coating, a preferred lubricant coating to provide the pharmaceutical package with lubricious surface quality is silicone oil ("silicone"). Silicones are inorganic polymers containing a silicon-oxygen backbone with side chains or groups attached to the silicon atoms. Silicones are also called polysiloxanes. One of the most commonly encountered polysiloxanes is polydimethylsiloxane ("PDMS"). Silicone properties can be varied extensively by modification of side chains, end group modification, backbone chain length, backbone and crosslinking of two or more polysiloxane monomers during polysiloxane synthesis. Taking trimethylsiloxane endcapped polydimethylsiloxane as a basic model polysiloxane,

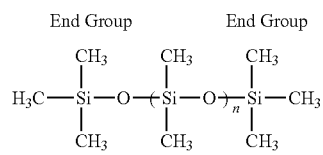

there are numerous modifications which can be made during polysiloxane synthesis using different siloxane monomers resulting in a silicone oil with desirable lubricant properties (e.g., viscosity, reactivity, hydrophobicity, etc.): side chain modification involves replacement of one or more methyl groups (—$CH_3$) with various functional groups such as —H, —CH=$Cl_2$, —$OCH_3$, —$CH_2CH_2CF_3$; endgroup modification involves replacement of one or more methyl groups with various reactive groups such as —OH, —CH=$CH_2$, —$OC(CH_2)CH_3$, —$OCH_3$, etc. for crosslinking purposes. A more comprehensive but non-exhaustive listing of siloxane monomers/polymers and a chemical discussion of polysiloxane chemistry can be found in Silicon Compounds: Silanes & Silicones Ed. Barry Arkles, Gerald Larson 2004, Gelest Inc. and Silicones in Pharmaceutical Applications André Colas, 2001, Dow Corning Healthcare Industries.

One special consideration for lubricants used in pharmaceutical packaging is the need for high chemical purity and low reactivity. In certain embodiments, this limits the type of polysiloxane that can be used due to purity that can be obtained due to the separation of desired lubricant from synthesis by-products. Another consideration is the desired properties of the lubricant (viscosity, crosslinking ability, lubricity, deposition neat or diluted, solubility in specific diluting solvents, etc.) the type of sterilization (e.g., steam sterilization such as autoclave, gamma irradiation, ethylene oxide sterilization and heat sterilization such as depyrogenation) it will undergo, and the type of surface to which it will be applied (e.g., glass, polymeric, metal; syringe bodies, syringe plungers, stoppers, needles, etc.). For pharmaceutical packaging use, polysiloxanes are sold under USP or medical grade purities. There are two types of polysiloxane formulations used for pharmaceutical packaging, those that have the lubricant already formed and those that form the lubricant prior to application. Examples of silicone oils and silicone oils with additives ready to apply with/without dilution to glass and polymeric surfaces would be Dow Corning 360 and Dow Corning 365 35% dimethicone NF emulsion. An example of a silicone oil ready to apply with/without dilution to metallic surfaces would be Dow Corning MDX4-4159 medical grade dispersion. Examples of polysiloxane formulations that form the lubricant prior to application are multiple component formulations. The most common types of formulations are to provide two (poly)siloxane components and crosslink them to provide a polysiloxane with the desired properties. Crosslinking can be accomplished via many types of curing reactions. The predominant crosslinking reactions employ platinum catalysts or peroxides for initiation. Physical methods are also used to enhance crosslinking such as exposure to electromagnetic radiation (ultraviolet—gamma rays) and heating. Vinyl end-capped siloxanes and hydrosiloxanes combined with a platinum catalyst are preferred species due to the purity of polysiloxane produced (only by-product is residual platinum in the part per million concentration level).

In a preferred embodiment of the invention the silicone oil lubricant that is used is made from the combination of multiple reactive polysiloxanes with a non-reactive polysiloxane as disclosed in U.S. Pat. No. 6,296,893. Other suitable silicone oils, preferred methods of application, and uses in pharmaceutical packaging are taught in U.S. Pat. No. 5,736,251, U.S. Pat. Nos. 5,338,312 and 6,461,334, which are herein incorporated by reference. U.S. Pat. No. 5,736,251 discloses silicone coatings and treatments which upon curing result in a three dimensional lubricant structure effective at reducing by 50-80% the coefficient of friction compared to uncoated surfaces. U.S. Pat. No. 5,338,312 discloses a first silicone crosslinked base layer and second silicone layer providing lubrication to an article. U.S. Pat. No. 6,461,334 discloses a silicon containing coating that is both lubricious and protein deterrent. U.S. Pat. Nos. 6,866,656, 6,461,334, U.S. Pat. No. 5,338,312, U.S. Pat. No. 5,736,251, U.S. Pat. No. 5,338,312, U.S. Pat. No. 6,461,334, U.S. Pat. No. 6,296,893, U.S. Pat. No. 4,822,632, WO 88/10130, Silanes & Silicones Ed. Barry Arkles, Gerald Larson 2004, Gelest Inc. and Silicones in Pharmaceutical Applications Andre Colas, 2001, are all incorporated by reference.

Fluorinated polymer compounds are another preferred class of suitable lubricants that can be used for the lubricious coating of the pharmaceutical packaging surface. Preferred lubricious compounds are, for example, the perfluorinated polyethers or fluorinated hydrocarbons disclosed in US Application 2004/0231926 and the lubricants disclosed in U.S. Pat. No. 6,645,483, both of which are hereby incorporated by reference.

In certain embodiments the lubricious coating (e.g., silicone or fluorinated polymer) is deposited over a functional coating such as a barrier coating (e.g., oxides such as $SiO_2$) or a coating that minimizes protein loss. Alternatively, the lubricious coating may be deposited under other functional coatings such as a barrier coatings (e.g., oxides such as $SiO_2$) or a coating that minimizes protein loss. The lubricious coating thickness can range from a monolayer to about 1000 nm. Preferably the lubricious coating is from about 1 to 700 nm; most preferably the lubricious coating is from about 1 to 500 nm.

There are many types of barrier coatings, which may be applied to pharmaceutical packaging surfaces that have the ability to retard, to varying extents, the permeation of gaseous species such as water vapor and carbon dioxide. These coating thereby provide protection to the substances stored within. Barrier coatings may also be applied to pharmaceutical packaging surface to retard, to varying extent, the leaching of components from the base substrate and/or the ion exchange of cations/anions with the base substrate. Preferred barrier coatings and methods of applying the barrier coatings are disclosed in DE 196 29 877, EP 08 210 79, DE 44 38 359, EP 07 094 85, and DE 296 09 958, and in US 2003/0134060, US 2004/0247948, US 2005/0227002, all hereby incorporated by reference. In certain embodiments the barrier coating (e.g., oxides such as $SiO_2$) is deposited over a coating that minimizes protein loss. Alternatively, the barrier coating (e.g., oxides such as $SiO_2$) is deposited under a coating that minimizes protein loss. Particularly preferred barrier coatings are those coatings that do not interfere with the protein deterrent functions of the coating that minimizes protein loss.

Preferred embodiments of this invention use a barrier coating with a coating that minimizes protein loss and a barrier coating with a coating that minimizes protein loss and a lubricious coating. In certain embodiments of the present invention, the barrier coating (e.g., oxides such as $SiO_2$) is deposited over another functional coating such as the lubricious coating or over the coating that minimizes protein loss. Alternatively, a barrier coating (e.g., oxides such as $SiO_2$) may be deposited under a coating such as the lubricous coating or the coating that minimizes protein loss. The barrier coating thickness can range from a monolayer to about 500 nm. Preferably the barrier coating is from about 5 to 500 nm; most preferably the lubricious coating is from about 10 to 300 nm. Barrier coatings of 5-200 nm are most preferred such as, for example, about a 100 nm barrier coating.

The various multi-functional coatings adhere to each other by a variety of mechanisms depending on the chosen coating. Without being bound by theory, the various coatings adhere by adsorption, physical entanglement, hydrogen bonding, covalent bonding, and electrostatic interaction.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. The entire disclosure[s] of all patent applications, patents, and papers cited herein are incorporated by reference herein.

EXAMPLES

1) Lubricious Coating Plus Coating that Minimizes Protein Loss.

A matrix of proteins and formulations is tested to establish the adsorption of proteins to various coated surfaces. These tests are conducted in syringes (Type 1 glass and COC polymer materials) by the methods disclosed in U.S. Application 60/617,192 titled "Multiplexed protein adsorption assay" where a coated surface can be exposed to multiple proteins under different conditions simultaneously. U.S. application 60/617,192 is incorporated by reference.

Fluorescently labeled (Cy-3 dye from Amersham) insulin and histone are used as two test proteins which are brought into contact with the interior surfaces of syringes in liquid formulations to investigate if protein deterrence could be accomplished, while at the same time maintaining lubricity. The interior surfaces of the syringes are sequentially coated by a coating that minimizes protein loss followed by a silicone oil coating. The protein deterrent hydrogel coating is taught in the examples of US 2004-0115721 and the compound is further modified by blocking. The lubricious silicone oil coating used in this example is taught in U.S. Pat. No. 6,296,893.

Six different coated articles are prepared: 1) TNS refers to Topas™ not siliconized, 2) TS refers to Topas™ siliconized, 3) TH refers to Topas™ with a hydrogel coating that minimizes protein loss, 4) THS refers to Topas™ with a hydrogel coating that minimizes protein loss followed by silicon oil coating, 5) GH refers to Type 1 glass with a hydrogel coating that minimizes protein loss, and 6) GHS refers to Type 1 glass with a hydrogel coating that minimizes protein loss followed by silicon oil coating. The results shown in FIG. 1 demonstrate that the protein deterrence exhibited by a hydrogel coating on Topas™ as well as Type I glass is maintained, even after a silicone oil coating is secondarily deposited for lubricity. This is a surprising result showing that the protein deterring ability of the protein deterring coating is maintained with the addition of a second coating to provide lubricity.

2) Lubricious Coating Plus Coating that Minimizes Protein Loss.

Example 1 is repeated with the addition of fluorescently labeled IgG and lysozyme to test a broader range of proteins. The results shown in FIG. 2 are similar to those shown in Example 1 which demonstrated that the protein deterrence exhibited by a hydrogel coating on Topas™ as well as Type 1 glass are maintained, even after a silicone oil coating is secondarily deposited for lubricity.

3) Lubricious Coating Plus Coating that Minimizes Protein Loss.

Syringes with a silicone oil coating are spray-coated with the hydrogel coating that minimizes protein loss used in Examples 1 and 2. Frictional force measurements are conducted using an Instron 5564 to determine the breakaway/sliding force profile of syringes with silicone oil coating compared to syringes with silicone oil coating plus coating that minimizes protein loss. The results shown in FIG. 3 demonstrate that the lubricity of both syringe types is statistically similar, as the standard deviation for each average force profile is ±1 newton. This is a surprising result that the lubricant properties of the lubricant coating are maintained with the addition of a protein deterrent coating layer beneath the lubricant coating layer.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

We claim:

1. A multi-functional pharmaceutical package comprising a pharmaceutical package surface coated with
   (a) a lubricious silicone oil coating or a lubricious fluorinated polymer coating and
   (b) a protein adsorption deterrent diglyme, triglyme, tetraglyme, pentaglyme or hexaglyme coating.

2. A multi-functional pharmaceutical package according to claim 1, wherein said surface further comprises a barrier layer coating.

3. A multi-functional pharmaceutical package according to claim 1, wherein said coatings are each independently deposited via spray coating, dip coating, chemical vapor deposition, plasma enhanced chemical vapor deposition, evaporation, sputtering, or ion-plating.

4. A multi-functional pharmaceutical package according to claim 1, wherein the pharmaceutical package comprises a vial, a plastic-coated vial, a syringe, a plastic coated syringe, an ampoule, a plastic coated ampoule, a cartridge, a bottle, a plastic coated bottle, a pouch, a pump, a sprayer, a stopper, a needle, a plunger, a cap, a stent, a catheter or an implant.

5. A multi-functional pharmaceutical package according to claim 1, wherein the pharmaceutical package surface is in contact with a pharmaceutical or biotechnological substance or formulation.

6. A multi-functional pharmaceutical package according to claim 1, further comprising an optical coating and/or a break resistant coating.

7. A multi-functional pharmaceutical package according to claim 1, wherein the pharmaceutical package comprises a Type 1 glass, a Type 2 glass, a Type 3 glass, a silicate glass, a borate glass, a borosilicate glass, a phosphate glass, a soda-lime silicate glass, a package with a siliconized surface or a package with a silanized surface.

8. A multi-functional pharmaceutical package according to claim 1, wherein the pharmaceutical package comprises acrylic, polycarbonate, polyester, polypropylene, polyacetal, polystyrene, polyamide, polyacrylamide, polyimide, polyolefin, cyclic olefin copolymer, rubber, an elastomer, a thermosetting polymer, a thermoplastic polymer, a metal or an alloy.

9. A multi-functional pharmaceutical package according to claim 1, wherein said protein deterrent coating reduces the adsorption of protein to said surface by at least about 25% compared to the adsorption on the uncoated surface.

10. A multi-functional pharmaceutical package according to claim 1, wherein said lubricious coating increases the lubricity of the surface by at least about 50% compared to the uncoated surface.

11. A multi-functional pharmaceutical package according to claim 1, wherein said protein adsorption deterrent-coating is a tetraglyme.

12. A multi-functional pharmaceutical package according to claim 1, wherein said surface has coatings consisting essentially of:
   (a) a lubricious silicone oil coating or a lubricious fluorinated polymer coating and
   (b) a protein adsorption deterrent diglyme, triglyme, tetraglyme, pentaglyme or hexaglyme coating.

13. A multi-functional pharmaceutical package according to claim 1, wherein said silicone oil is a medical grade PDMS or a derivative thereof.

14. A multi-functional pharmaceutical package according to claim 1, wherein said lubricious fluorinated polymer coating is a perfluorinated polyether or a fluorinated hydrocarbon.

15. A multi-functional pharmaceutical package according to claim 1, further comprising a polymer coating comprising silicon, oxygen, carbon and hydrogen.

16. A multi-functional pharmaceutical package according to claim 2, wherein said barrier coating is $SiO_2$, $Al_2O_3$, $ZrO_2$ or $TiO_2$.

17. A multi-functional pharmaceutical package according to claim 1, wherein said lubricious silicone oil is made from the combination of multiple reactive polysilaxanes with a non-reactive polysiloxane.

18. A multi-functional pharmaceutical package comprising a pharmaceutical package surface coated with
   (a) an anti-adherency coating comprising silicon, oxygen, carbon and hydrogen and
   (b) a protein adsorption deterrent diglyme, triglyme, tetraglyme, pentaglyme or hexaglyme.

19. A multi-functional pharmaceutical package comprising a pharmaceutical package surface coated with
   (a) a lubricious oil, wax or fat coating
   and
   (b) a protein adsorption deterrent diglyme, triglyme, tetraglyme, pentaglyme or hexaglyme.

20. A multi-functional pharmaceutical package comprising
   a pharmaceutical package surface coated with
     (a) a barrier coating
     and
     (b) a protein adsorption deterrent diglyme, triglyme, tetraglyme, pentaglyme or hexaglyme coating.

21. A multi-functional pharmaceutical package according to claim 20, wherein said barrier coating comprises $SiO_2$, $Al_2O_3$, $ZrO_2$ or $TiO_2$.

22. A multi-functional pharmaceutical package according to claim 1, comprising:
   a lubricious silicone oil made from the combination of multiple reactive polysiloxanes with a non-reactive polysiloxane and a protein deterrent hydrogel coating over said silicon oil coating.

23. A method of preparing a multi-functional pharmaceutical package comprising:
   depositing a protein adsorption deterrent diglyme, triglyme, tetraglyme, pentaglyme or hexaglyme coating
   and
   depositing a lubricious silicone oil or lubricous fluorinated polymer coating onto the surface of a pharmaceutical package.

24. A method according to claim 23, further comprising depositing a barrier layer coating.

25. A method according to claim 23, wherein the pharmaceutical package is a vial, a plastic-coated vial, a syringe, a plastic coated syringe, an ampoule, a plastic coated ampoule, a cartridge, a bottle, a plastic coated bottle, a pouch, a pump, a sprayer, a stopper, a needle, a plunger, a cap, a stent, a catheter or an implant.

26. A method according to claim 23, wherein the pharmaceutical package or components thereof that come in contact with a pharmaceutical or biotechnological substance or formulation.

27. A method according to claim 23, wherein the pharmaceutical package comprises Type 1 glass, a Type 2 glass, a Type 3 glass, a silicate glass, a borate glass, a borosilicate glass, a phosphate glass or a soda-lime silicate glass.

28. A method according to claim 23, wherein the pharmaceutical package comprises acrylic, polycarbonate, polyester, polypropylene, polyacetal, polystyrene, polyamide, polyacrylamide, polyimide, polyolefin, cyclic olefin copolymer, rubber, an elastomer, a thermosetting polymer, a thermoplastic polymer, metal or a metal alloy.

29. A method according to claim 23, wherein said coating that minimizes protein loss reduces the adsorption of protein to said surface by at least about 25% compared to the adsorption on the uncoated surface.

30. A method according to claim 23, wherein said protein adsorption deterrent coating is a tetraglyme.

31. A method of preparing a multi-functional surface on a pharmaceutical package comprising:
   depositing a barrier coating onto the surface of said pharmaceutical package and
   depositing a lubricious silicone oil or lubricous fluorinated polymer coating onto the surface of a pharmaceutical package
   and
   depositing a protein adsorption deterrent diglyme, triglyme, tetraglyme, pentaglyme or hexaglyme coating onto the surface of a pharmaceutical package.

32. A method according to claim 23, comprising:
   depositing a lubricious silicone oil made from the combination of multiple reactive polysiloxanes with a non-reactive polysiloxane onto a surface of a pharmaceutical package by spraying,
   baking said silicon oil coating and depositing a subsequent protein adsorption deterrent diglyme, triglyme, tetraglyme, pentaglyme or hexaglyme coating over said silicon oil coating.

33. A method according to claim 23, wherein said lubricious silicone oil is PDMS or a derivative thereof.

34. A method according to claim 23, wherein said lubricious silicone oil is made from the combination of multiple reactive polysiloxanes with a non-reactive polysiloxane.

35. A method according to claim 21, wherein said lubricious fluorinated polymer coatings is a perfluoropolyether or a fluorinated hydrocarbon.

36. A method of preparing a multi-functional surface on a pharmaceutical package comprising:
   depositing a protein adsorption deterrent diglyme, triglyme, tetraglyme, pentaglyme or hexaglyme coating onto the surface of a pharmaceutical package
   and
   depositing a barrier coating
   onto the surface of said pharmaceutical package.

37. A method of preparing a multi-functional surface on a pharmaceutical package according to claim 36, wherein said barrier coating comprises $SiO_2$, $Al_2O_3$, $ZrO_2$ or $TiO_2$.

* * * * *

UNITED STATES PATENT AND TRADEMARK OFFICE
CERTIFICATE OF CORRECTION

| | |
|---|---|
| PATENT NO. | : 8,323,166 B2 |
| APPLICATION NO. | : 12/160259 |
| DATED | : December 4, 2012 |
| INVENTOR(S) | : Haines et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this
Fifth Day of August, 2014

Michelle K. Lee
*Deputy Director of the United States Patent and Trademark Office*